United States Patent [19]

Mikoshiba et al.

[11] 4,448,525
[45] May 15, 1984

[54] CRYSTAL DEFECTS ANALYZER

[75] Inventors: Nobuo Mikoshiba; Kazuo Tsubouchi; Kenji Wasa, all of Sendai, Japan

[73] Assignee: Semiconductor Research Foundation, Miyagi, Japan

[21] Appl. No.: 277,645

[22] Filed: Jun. 26, 1981

[30] Foreign Application Priority Data

Jun. 27, 1980 [JP] Japan .................................. 55-88099

[51] Int. Cl.³ ...................... G01N 21/00; G01N 29/04
[52] U.S. Cl. .......................................... 356/73; 73/607; 73/643; 356/237; 367/165
[58] Field of Search ................................. 356/72, 237; 73/606–607, 643, DIG. 4, 632, 644, 571, 24, 633–642, 603–605, 608, 584, 598, 593, 595, 600–602, 570; 358/112; 350/358; 310/336; 367/7–8, 11, 165

[56] References Cited

U.S. PATENT DOCUMENTS

| | | | |
|---|---|---|---|
| 2,711,646 | 6/1955 | Mendousse | 310/336 |
| 2,885,887 | 5/1959 | Hanysz | 73/600 |
| 2,912,853 | 11/1959 | Hanysz | 73/642 |
| 3,126,579 | 3/1964 | Janszen | 73/584 |
| 3,431,462 | 3/1969 | Muenow et al. | 367/165 |
| 3,903,733 | 9/1975 | Murayama et al. | 73/DIG. 4 |
| 4,276,780 | 7/1981 | Patel et al. | 73/643 |

OTHER PUBLICATIONS

Gutfeld et al., "20-MHz Acoustic Waves from Pulsed Thermoelastic Expansions of Constrained Surfaces", Appl. Phys. Letts. 3-1977, pp. 257-258.

Rosencwaig et al., "Photoacoustic Study of Laser Damage in Thin Films", Appl. Phys. Lett. 4-1980, pp. 667-669.

Busse et al., "Subsurface Imaging with Photoacoustics" App. Phys. Lett. 36(10) May 15, 1980, pp. 815-816.

Farrow et al., "Piezoelectric Detection of Photoacoustic Signals" App. Optics, 4-1-78, pp. 1093-1098.

Primary Examiner—William H. Punter
Attorney, Agent, or Firm—Robert E. Burns; Emmanuel J. Lobato; Bruce L. Adams

[57] ABSTRACT

A crystal defect analyzer comprises acousto-electric transducer means disposed in close adherence to a sample to be analyzed through the medium of a filter layer which functions to intercept light or electrons or particles emitted from said excitation means and to transmit only acoustic waves produced within said sample by excitation, thereby it can attain higher response and sensitivity, smaller size, higher resistance to vibration and superior operationality.

24 Claims, 36 Drawing Figures

CRYSTAL DEFECTS ANALYZER

BACKGROUND OF THE INVENTION

This invention relates to a defects analyzer for solid materials.

In 1880 a photoacoustic effect was discovered by Alexander Graham Bell and its application has recently been reconsidered, and a photoacoustic spectrometer (hereinafter referred to simply as "PAS") is known as an example of an analyzer of this sort. According to the prior art, analyzers of this sort are manufactured on the basis of the following principle. When light is irradiated upon a substance, the substance absorbs the light and becomes excited. The excitation energy goes through (1) Photochemical reaction, (2) light emission and (3) non-radiative transition, and then returns to the ground level. In this case, when going through the non-radiative transition of the above (3), there occurs a thermal change within the substance since there is no place of escape of the energy. If, in this case, the light is modulated in amplitude, such thermal change exhibits a periodic change dependent upon the modulation frequency and the gas sealed in the sample cell also undergoes a similar periodic pressure change resulting in the occurrence of an acoustic wave within the gas. This acoustic wave is detected by a microphone and its PA (photoacoustic) spectrum is observed.

Consequently, the PAS according to the foregoing prior art has the following drawbacks.

(1) Since a microphone is used, acoustic waves to be detected are limited to those of low frequencies of the order of 10 Hz to 2 kHz, which is quite insufficient to measure the relaxation time from the excited state in solid.

(2) Because a microphone is used, it is necessary to avoid vibration as far as possible and a sample must be set within a sealed gas cell. Consequently, great difficulties are encountered in operation.

(3) Because a microphone is used, there must be adopted the technique of detecting an acoustic wave occurring from the surface of a solid into a gas. When the difference in density between solid and gas is taken into account, this method is very inefficient. Consequently, this method requires a very strong light source.

(4) Because a microphone is used, the apparatus cannot be used in vacuum, and consequently an electron ray or corpuscular ray is not employable as the source of excitation energy.

(5) Since it is necessary to produce a thermal change induced by light on the surface of a sample, the light must be sure to be chopped or modulated in amplitude.

It is the object of this invention to provide a crystal defects analyzer including acousto-electric transducer means disposed in close adherence to a sample to be analyzed through the medium of a filter layer whereby the foregoing drawbacks associated with the prior art are eliminated and there are attained high response, high sensitivity, compact size, vibration resistance and superior operationality.

SUMMARY OF THE INVENTION

The apparatus of this invention, therefore, comprises excitation means for exciting a sample to be analyzed and acousto-electric transducer means disposed in close adherence to said sample through the medium of a filter layer, said filter layer functioning to intercept light or electrons or particles emitted from said excitation means and to transmit only acoustic waves produced within said sample by said excitation.

Also, the apparatus of this invention comprises excitation means for exciting a sample to be analyzed, acousto-electric transducer means disposed in close adherence to said sample through the medium of a filter layer, said filter layer functioning to intercept light or electrons or particles emitted from said excitation means and to transmit only acoustic waves produced within said sample by said excitation, further, for the measurement of photoluminescence, another excitation means for irradiating the surface of said sample, and a photo detector means for detecting a photoluminescence produced upon irradiation by said another excitation means.

DESCRIPTION OF THE PREFERRED EMBODIMENTS

This invention will be described in detail hereafter with reference to the accompanying drawings.

Figure 1:
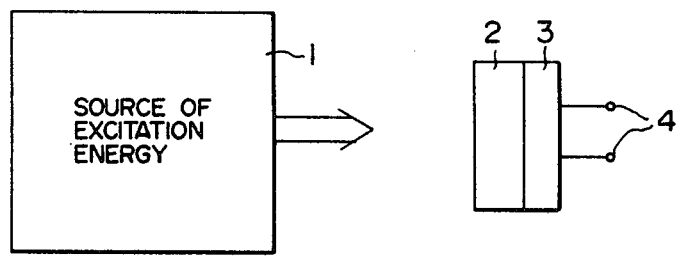
FIG. 1 illustrates the principle of a crystal defects analyzer.

Referring to FIG. 1, which illustrates the principle of the invention, the reference numeral 1 is a source of excitation energy for exciting the electrons in a sample, numeral 2 is a sample to be analyzed, numeral 3 is a solid-state acousto-electric transducer as acousto-electric conversion means disposed in close adherence to the sample, and numeral 4 is an electrical output terminal. The solid-state acousto-electric transducer 3 includes a bonding layer and a shielding layer as a filter layer both as will be described later.

The feature of this invention resides in that the solid-state acousto-electric transducer 3 is disposed in close adherence to a sample to be analyzed through the medium of a filter layer. Unlike the prior art, the interposition of gas is not needed.

Figure 2:
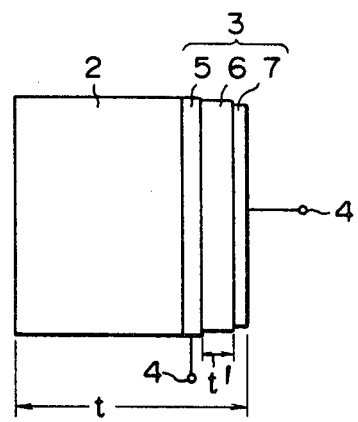
FIGS. 2 and 4 through 7 illustrate embodiments of the combination of a sample and a solid-state acousto-electric transducer.

Referring now to FIG. 2, there is shown an embodiment of the combination of a sample and a solid-state acousto-electric transducer disposed in close adherence thereto, wherein the reference numeral 2 is a sample to be analyzed and numeral 3 is a solid-state acousto-electric transducer having the following structure.

Numeral 5 designates a conductor layer serving as a filter layer for intercepting light, electrons, or particles as irradiated from the source of excitation energy 1 and transmitted through the sample and allowing only acoustic waves produced in the sample to pass therethrough, and also as one electrical output terminal. Particularly when the source of excitation energy 1 is electrons or charged particles, there flows an absorption current in the sample 2, so it is necessary either to suppress as far as possible the induction to an electrical output terminal 4 connected to the layer 7 by connecting the shielding conductor layer 5 to ground, or to provide an arithmetic circuit (not shown) for subtracting the absorption current in advance. Numeral 6 designates a piezo-electric layer for acousto-electric conversion, and numeral 7 is a conductor layer providing the other electrical output terminal. The piezo-electric layer 6 is provided for converting an acoustic wave produced in a solid into an electrical signal; and as piezo-electric materials there may be used, for example, ZnO, AlN, GaAs, GaP, GaSb, InAs, InP, InSb, Se, Te, CdS, ZnS, PZT system ceramics [Pb(Sr$_{0.5}$So$_{0.5}$)O$_3$, PbZrO$_3$, PbTiO$_3$, etc.], $\gamma$-Bi$_2$O$_3$ series compounds (Bi$_{12}$GeO$_{20}$, Bi$_{12}$PbO$_{19}$, Bi$_{12}$SiO$_{20}$), LiNbO$_3$, LiTaO$_3$, and quartz crystal, among which ZnO, AlN, CdS and PZT system ceramics are particularly preferred. These piezo-electric materials may be used as a mixture of two or more.

As the conductor in the conductor layers 5 and 7 there may be used such metals as Al, Au, Ag, Cu, Cr, Mo, In and Pb, or electrically conductive coating materials. Two or more of these conductors may be used in combination.

The thickness t' of the piezo-electric layer 6 is set in the following manner. The acoustic velocity of the piezo-electric layer, the frequency of an acoustic wave to be detected and the wave length thereof are assumed to be v', f$_a$ and $\lambda_a$, respectively. When t' is selected so as to satisfy the following equation, the resonance center frequency f$_o$ of the piezo-electric layer itself and f$_a$ coincide and constitute a guideline for an efficient detection.

$$t' = \frac{\lambda_a}{2} = \frac{v'}{2f_a} \qquad (1)$$

Figure 3A:
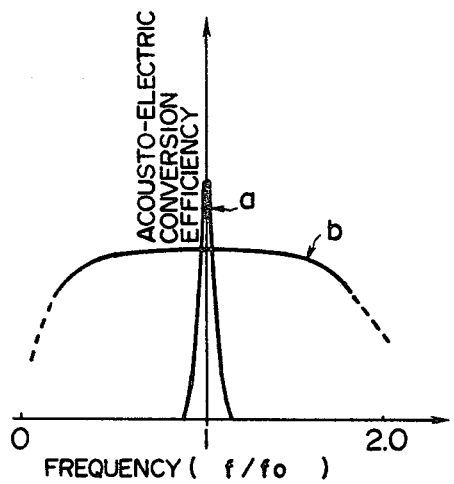
FIG. 3(a) illustrates the acousto-electric conversion efficiency of an acousto-electric transducer alone.
Figure 3B:
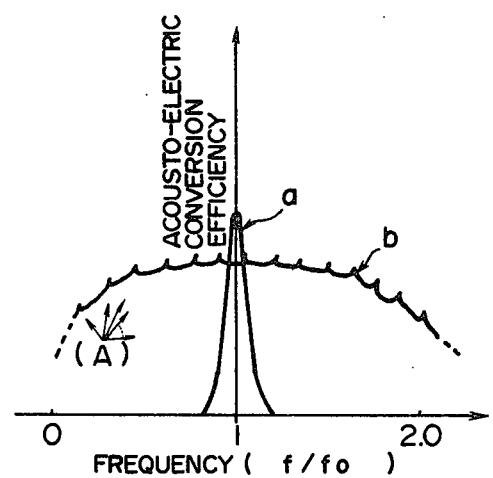
FIG. 3(b) illustrates the acousto-electric conversion efficiency of the acousto-electric transducer bonded with a sample.

If the piezo-electric layer 6 and the sample 2 are close to each other as shown in FIG. 2, the frequency characteristic of the acousto-electric conversion efficiency becomes a very broad-band characteristic and the acousto-electric conversion efficiency so much decreases as shown in FIG. 3. However, acoustic waves produced from samples contain frequency components of a very broad band, therefore, as shown in FIG. 3, the broad band formed by such a close adherence results in improvement of the detecting capability. The row of peaks shown in (A) of Fig. 3(b) comes out at intervals of $\Delta f = v/2t$ if acoustic wave is propagated at an average velocity v through the thickness t shown in Fig. 2 and sample 1 and acousto-electric transducer 3 are parallel. In FIGS. 3(a) and 3(b), the reference numeral a indicates a characteristic of the only acousto-electric transducer 3 and the reference numeral b indicates a characteristic of the acousto-electric transducer 3 bonded with the sample 2.

The conductor layers 5 and 7 are desired to be as thin as possible, provided they should retain an electrical conductivity for detecting acoustic waves efficiently and retain a shielding effect against the source of excitation energy. For example, it is desired that the lower limit of the thickness be on the order of several hundred to several thousand Å and that the upper limit be one for several of the thickness t' of the piezo-electric layer 6.

Figure 4:
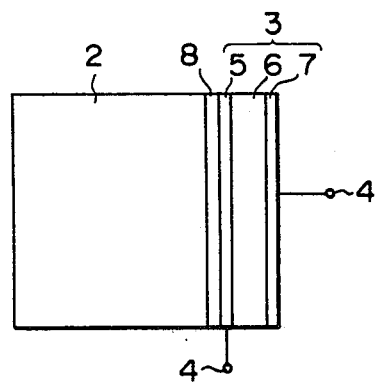

In the embodiment shown in FIG. 2, the conductor layer 5 serves both as a shield against the source of excitation energy and as one electrical output terminal, while in FIG. 4 both are separated. In the acousto-electric transducer shown in FIG. 4, a shielding layer 8 as a filter layer is formed on the back of a sample to be analyzed, which layer may be formed of any material affording the shielding effect, provided it should be kept in close elastic contact with the sample. For example, there may be used metals, coating materials, waxes, pastes and greases. The shielding layer 8 is desired to be as thin as possible, provided it should retain the shielding effect.

The method for close adherence between the sample 2 to be analyzed and the solid-state acousto-electric transducer 3 will be described hereinunder. By the close adherence of the two there must be created an acoustically coupled state to introduce an acoustic wave produced in the sample 2 into the solid-state acousto-electric transducer 3.

In the embodiment shown in FIG. 2, the conductor layer 5 serves as an acoustic coupler. This construction is attainable, for example, by successively forming on the sample 2, the conductor layer 5, the piezo-electric layer 6 and the conductor layer 7 according to a known technique such as evaporation, sputtering, or CVD. Alternatively, the solid-state acousto-electric transducer 3 may be formed in advance and the conductor layer 5 is formed of a low melting conductor such as In, or the surface of the conductor layer 5 or the surface of the sample 2 may be covered with a low melting conductor, then the sample 2 and the solid-state acousto-electric transducer 3 are coupled together by thermo compression bonding.

In the embodiment shown in FIG. 4, the shielding layer 8 serves as an acoustic coupler. This construction is attainable, for example, by successively forming on the sample 2 the shielding layer 8, the conductor layer 5, the piezo-electric layer 6 and the conductor layer 7 according to a known technique such as evaporation, sputtering, or CVD. Alternatively, the portions indicated with numerals 5, 6 and 7 of the solid-state acousto-electric transducer 3 may be formed in advance, then the shielding layer 8 is formed on the surface of either the sample 2 or the portion 5 of the solid-state acousto-electric transducer 3 according to a known technique such as evaporation or application, and thereafter the two are coupled together by thermo compression bonding.

The method for adhesion between the sample 2 and the portions indicated with numerals 5, 6 and 7 of the solid-state acousto-electric transducer 3 as set forth above with reference to FIGS. 2 and 4 can be made simpler in the following manner.

Figure 5:
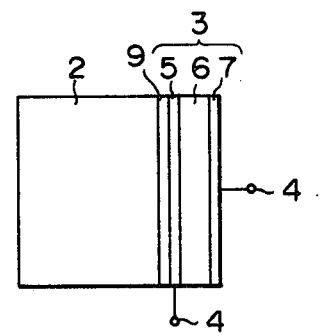

In the embodiment shown in FIG. 5, the sample 2 and the portions indicated with numerals 5, 6, 7 of the solid-state acousto-electric transducer 3 have been prepared each independently and coupled together acoustically by a bonding layer 9. As the bonding layer 9, a low melting metal or alloy may be evaporated or applied followed by thermo compression bonding, or for the adhesion there may be used coating materials, adhesives, greases, pastes, or waxes, provided the materials selected should avoid the production of an acoustic wave by the source of excitation energy in the bonding layer 9 to prevent the provision of a noise source. For example, when a light source in the visible region was used as the source of excitation energy, an ordinary silver paste generated a very large noise, while good characteristics were obtained in the use of electron wax.

It is desirable that the thickness of the bonding layer 9 be one for several of the thickness $t'$ of the piezo-electric layer 6.

Figure 6:
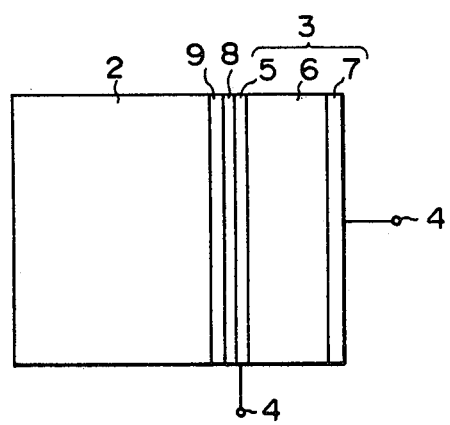

In the embodiment shown in FIG. 6, the sample 2 and the portions indicated with numerals 5, 6, 7 of the solid-state acousto-electric transducer 3 including the shielding layer 8 have been prepared each independently and coupled together acoustically by the bonding layer 9. The same precautions as mentioned in connection with the embodiment of FIG. 5 should be taken about the material and thickness of the bonding layer 9.

Figure 7A:
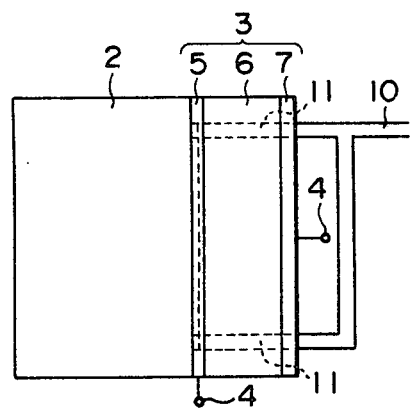
Figure 7B:
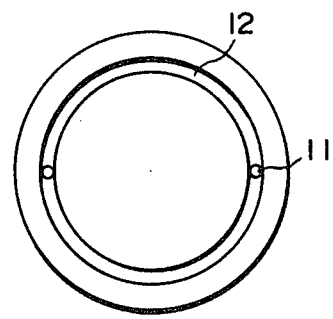

If one side of the sample 2 to be accoustically connected to the solid-state acousto-electric transducer 3 is a flat mirror surface, the acoustic coupling is attainable by vacuum chuck as illustrated in FIG. 7. In FIG. 7(a), a vacuum pipe 10 is connected to a vacuum system for vacuum connection through holes 11 formed in the solid-state acousto-electric transducer 3. FIG. 7(b) shows an example of arrangement of the holes 11 and grooves 12 for vacuum suction formed in the surface in close adherence to the sample 2 of the solid-state acousto-electric transducer 3.

The vacuum suction grooves 12 and holes 11 may be provided so as not to largely diminish the surface of the sample 2, but in sufficient numbers for the acoustic coupling, with their shapes and arrangement being optional. The vacuum pipe 10 is formed of a soft material such as vinyl, nylon or other synthetic resin to avoid acoustic loss.

According to one of the means embodied in FIGS. 2 and 4 through 7, the solid-state acousto-electric transducer 3 in close adherence to the sample 2 to be analyzed is mounted on a jig, but in this case care must be exercised to avoid loss of a faint acoustic wave caused by contact with the jig or causes of noise such as reflection and resonance in order to detect the faint acoustic wave.

Figure 8A:
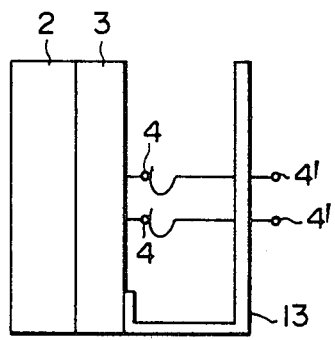
FIG. 8(a) illustrates an embodiment of the combination of a L-shaped jig, a sample and a solid-state acousto-electric transducer.

The jig illustrated in FIG. 8(a) is constructed so that only a very limited portion of the solid-state acousto-electric transducer 3 in close adherence to the sample 2 to be analyzed is mounted and fixed on the jig 13. The electrical output terminals 4 are electrically connected through fine conductors to electrical output terminals 4' of the jig.

Figure 8B:
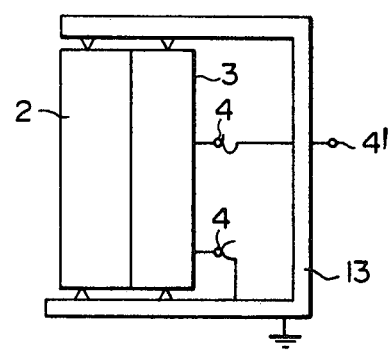
FIG. 8(b) illustrates an embodiment of the combination of a ]-shaped jig, a sample and a solid-state acousto-electric transducer.

The jig embodied in FIG. 8(b) is characteristic in that the acoustic coupling with the jig of both the sample 2 and the solid-state acousto-electric transducer 3 is minimized without affecting the resistance to mechanical vibration of the entire apparatus.

Again it is to be noted that for attaining a close adherence of the solid-state acousto-electric transducer 3 to the sample 2 to be analyzed there may be used any of the means embodied in FIGS. 2 and 4 through 7 or even other means, provided the sample 2 and the transducer 3 are shielded at an area intermediate between the two against the source of excitation energy and are accoustically connected together. Once the sample 2 and the solid-state acousto-electric transducer 3 are brought to a close adherence to each other in the manner mentioned above, both are then mounted on a jig so as to minimize their acoustic coupling with respect to the jig.

The sample 2 which has been brought to a close adherence to the solid-state acousto-electric transducer 3 by any of the means embodied in FIGS. 2 and 4 through 7 or by other means and which has been mounted on the jig in the manner illustrated in FIG. 8 or by other means, can now be evaluated in the crystal defects analyzer of FIG. 1.

Figure 9:
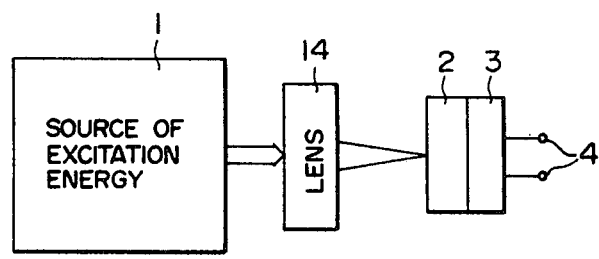
FIGS. 9 through 13 each illustrates an embodiment of a crystal defects analyzer including a source of excitation energy.

In the embodiment shown in FIG. 9, light, electrons, particles, or a combination thereof emitted from the source of excitation energy 1 is converged into beamlike by an optical lens 14 or an electrical (electrostatic or magnetostatic) lens and irradiated upon the surface of the sample. Such a beam formation permits the use of a small-sized source of excitation energy for a more sensitive crystal defects analyzer.

Figure 10:
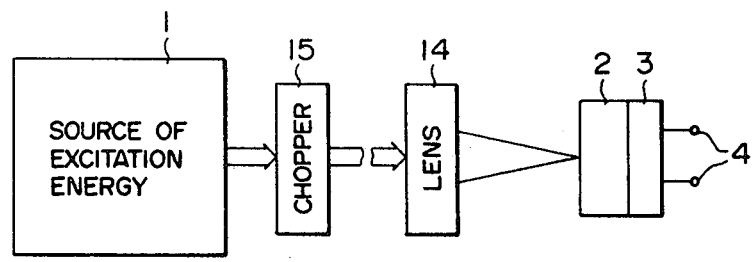

In the embodiment shown in FIG. 10, light, electrons, particles, or a combination thereof emitted from the source of excitation energy 1 is rendered intermittent by a chopper 15. Signals were output from the electrical output terminals 4 in correlation with chopping time intervals. The adoption of chopping contributed to an increase in sensitivity, a decrease of noise, and further permitted checking of the time response characteristic of crystal defects.

The chopper 15 may be disposed either before or after the lens 14, and the lens 14 may be omitted. There may be used any of optical, electrical, magnetical and mechanical chopping means. Conventional gas cell type apparatus have averted the use of a mechanical chopper, but by means of the apparatus of this invention there could be detected signals with high sensitivity even in the use of a mechanical chopper because the apparatus of the invention is little affected by vibrations. The purpose of chopping is attained if not only the source of excitation source is turned on and off in a perfect manner but also there can be performed a periodic amplitude modulation.

As to the relationship between the amplitude modulation frequency and the frequency characteristic of the solid-state acousto-electric transducer, as previously noted in connection with FIG. 3, the acousto-electric conversion characteristic becomes a broad-band characteristic upon a close adherence of the transducer 3 to the sample 2, so the detection of acoustic waves can be done discretely or continuously over from the amplitude modulation frequency up to an integer multiple of many of the modulation frequency.

Furthermore, since the acousto-electric conversion efficiency is over a broad band, it is not necessary to have the resonance frequency $f_o$ of only the solid-state acousto-electric transducer 3 coincident with the modulation frequency or an integer multiple thereof.

Figure 11:
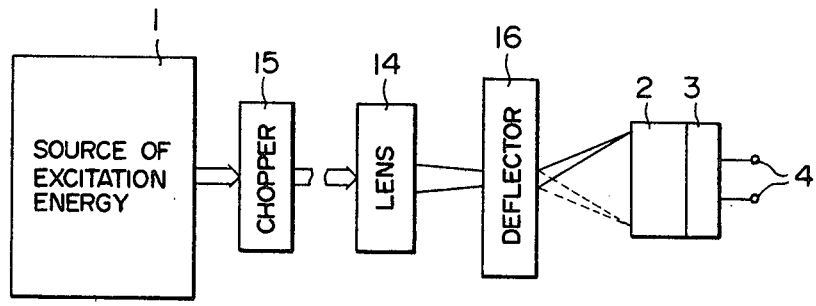

The embodiment shown in FIG. 11 is for checking a spatial distribution of crystal defects of the sample 2 to be analyzed, wherein light, electron, particles, or a combination thereof emitted from the source of excitation energy is made beam-like by the lens 14 and is allowed to scan the surface of the sample by a deflector 16. The deflector may utilize any of mechanical, optical, electrical and magnetical means, or a combination thereof.

Although the chopper 15 is used in the embodiment shown in FIG. 11, it may be omitted. And the deflector 16 may be positioned either before or after the lens 14.

Figure 12:
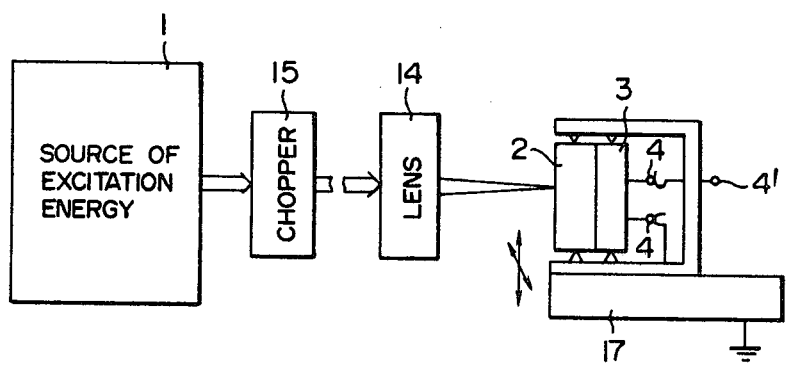

The embodiment shown in FIG. 12 is for checking a spatial distribution of crystal defects of the sample 2 to be analyzed, wherein light, electrons, particles, or a combination thereof emitted from the source of excitation energy 1 is rendered beam-like by the lens 14 and converged as a small spot onto the surface of the sample.

A manipulator 17 is scanned mechanically whereby a beam spot is allowed to scan on the surface of the sample. Conventional gas cell type apparatus have disliked a mechanical scanning to avoid the influence of vibration as far as possible, while the apparatus of this invention permits an effective use of a mechanical scanning since it is little influenced by vibrations.

The deflector 16 shown in FIG. 11 and the mechanical scanning mechanism shown in FIG. 12 may be used in combination.

Figure 13:
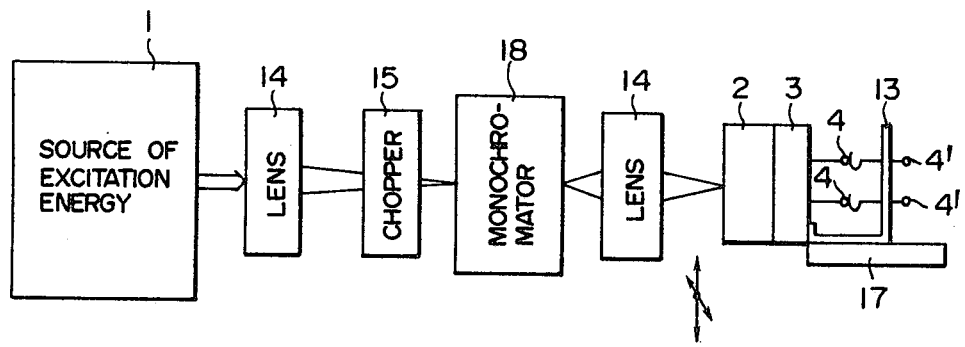

The crystal defects analyzer shown in FIG. 13 is for checking the energy distribution of crystal defects, wherein light, electrons, particles, or a combination thereof emitted from the source of excitation energy 1 is passed through a monochromator 18 to render the excitation energy variable. The lens 14 and the chopper 15 both are used in FIG. 13 to improve sensitivity, but they may be omitted. And although the mechanical scanning mechanism 17 is used to measure the spatial distribution, it may be substituted by the deflector 16 as shown in FIG. 11. According to the embodiment shown in FIG. 13 there were obtained data on both spatial distribution of crystal defects and energy distribution thereof. The spectroscope for light, electrons, or particles may utilize any of optical, electrical and magnetical means if only the excitation energy is rendered variable thereby.

An example of manufacturing method for the crystal defects analyzer of this invention will be described hereunder with reference to the drawings.

Figure 14A:
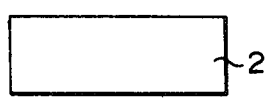
FIG. 14(a) through 14(d) illustrate an example of a method of maufacturing the combination of a sample and a solid-state acousto-electric transducer.

The crystal defects analyzer to be manufactured is the type shown in FIG. 2. Reference is first made to FIG. 14(a), wherein CdS and Si are used as the sample 2 to be analyzed, about 1 cm by 1 cm in area and several 100 $\mu$m to several mm in thickness, and its surface is made flat with #2000 to #4000 carborundum and sometimes if further finished to a mirror surface of about 1.0 $\mu$m to 0.3 $\mu$m.

Figure 14B:
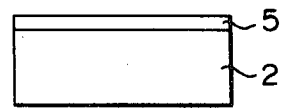
Figure 14C:
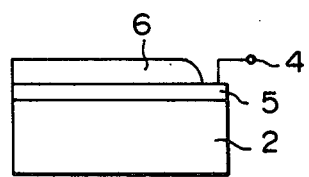

Next, as shown in FIG. 14(b), aluminum was evaporated on the sample 2 in a thickness of about 3000 to 5000 Å while maintaining the temperature of the sample 2 at about 150° C. Then, as shown in FIG. 14(c), using a mask (stainless steel mask) there was formed the piezo-electric layer 6 of ZnO about several $\mu$m to several 10 $\mu$m in thickness at a substrate temperature of about 180° C. according to the d.c. sputtering method so that the conductor layer 5 (aluminum) serving also as a shielding layer became partially exposed to form one of the electrical output terminals 4.

Figure 14D:
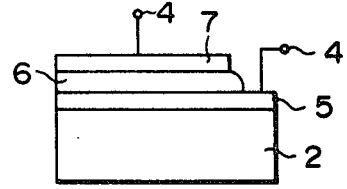

Furthermore, as shown in FIG. 14(d), aluminum was evaporated in a thickness of about 3000 to 5000 Å using a mask (stainless steel mask) at a substrate temperature of about 150° C. to form the conductor layer 7 on the piezo-electric layer 6 and the another electrical output terminal 4.

The total thickness of the filter layer and the acousto-electric transducer does not exceed about 100 microns and the total thickness of the sample, the filter layer and the acousto-electric transducer does not exceed about 1 mm.

As shown in the manufacturing example of FIG. 14, the solid-state acousto-electric transducer disposed in close adherence to the sample was, as an example, mounted on the jig (made of aluminum or brass) shown in FIG. 8(a) by adhering and fixing thereto the portion of the conductor layer 5 in FIG. 14(d) using a silver paste, and so one of the electrical output terminals (connected to the layer 5) was connected to ground. The electrical output terminal from the conductor layer 7 was taken out through an aluminum wire or copper wire of about 100 $\mu$m in diameter.

Figure 15:
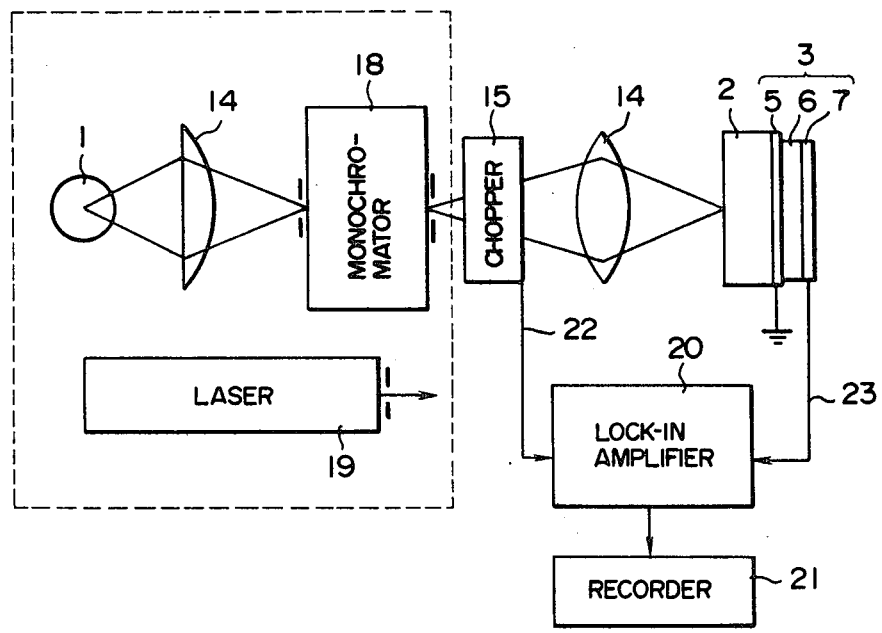
FIG. 15 illustrates an embodiment of a crystal defects analyzer.

The sample thus mounted on the jig in its adhered state closely to the solid-state acousto-electric transducer was, as an example, evaluated by the crystal defects analyzer shown in FIG. 15 wherein numerals 19 through 23 indicate respectively a laser, a lock-in amplifier, a recorder, a synchronous signal from the chopper 15, and a photoacoustic signal. The lock-in amplifier 20 is used for detecting the photoacoustic signal supplied by the sample 2, the signal having interrelation to the intermittent frequency of the source of excitation energy 1. As an example, moreover, using a 500 W xenon lamp, a light beam was condensed to below 100 $\mu$m through a lens system with a focal point of about 10 cm, passed through a spectroscope with a resolution of about 20 Å to 30 Å and subjected to measurements at a chop frequency of the chopper of about 300 Hz. As a result of evaluation of a CdS sample (a product of Eagle Pitcher Co., Grade A) there were obtained energy distribution and spatial distribution of crystal defects at a sensitivity of several $\mu$V to several 100 $\mu$V in terms of detected signal intensity.

Figure 16:
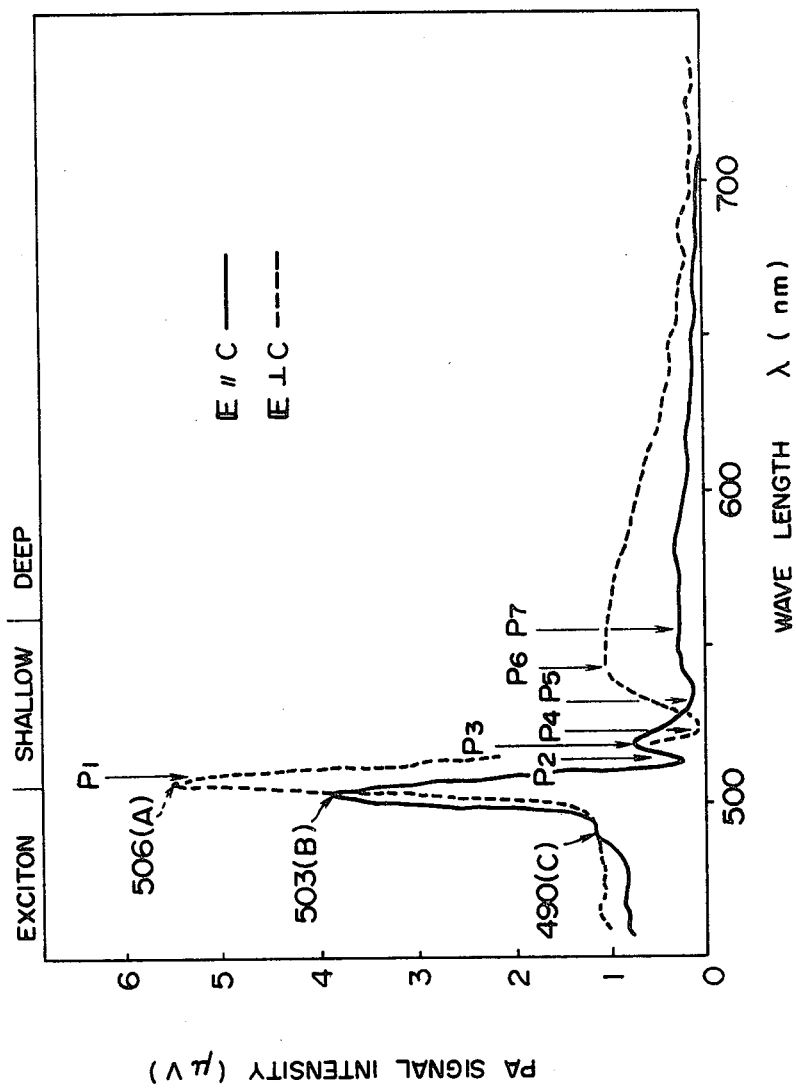
FIG. 16 illustrates an energy distribution of crystal defects obtained by the apparatus of this invention.

FIG. 16 shows data on detected photoacoustic signal intensity versus excitation light wave length characteristics. As will be apparent from the data, CdS has an energy gap of about 500 nm (about 2.5 eV) at room temperature, but at above the energy gap (i.e. on the short wave length side) there were observed peaks of A, B, C excitons. Also, in the vicinity of the gap below the energy gap (i.e. on the long wave length side) there were observed defect peaks and dips $P_1-P_7$ of a shallow level.

As to observation means for defect peaks, the method of this invention using the apparatus shown in FIG. 15 was compared with the conventional photoconductivity and photoluminescence methods, the results of which are set out in Table 1.

TABLE 1

The values of wave length corresponding to the light absorption due to seven states in CdS measured by various methods (units: nm)

|  | Photoconductivity | Photoluminescence | PAS | Nature |
|---|---|---|---|---|
| $P_1$ | 507.5 | ... | 509 | nonradiative |
| $P_2$ | 513.5 | 514 | 513 | radiative |
| $P_3$ | 517 | ... | 518 | nonradiative |
| $P_4$ | 522.5 | 524 | 523 | radiative |
| $P_5$ | 532 | 531 | 534 | radiative |
| $P_6$ | 542 | ... | 544 | nonradiative |
| $P_7$ | 555 | ... | 554 | nonradiative |

According to the photoconductivity method there were observed all the defect peaks $P_1-P_7$, but it is indistinguishable whether these defects are radiative or nonradiative. According to the photoluminescence method there were observed only radiative defects and the peaks $P_2$, $P_4$, $P_5$ were obtained. On the other hand, according to the method of this invention, as shown in FIG. 16, there were observed peaks at $P_1$, $P_3$, $P_6$ and $P_7$ and these defects proved to be nonradiative; furthermore, as illustrated in FIG. 16, dips were observed at $P_2$, $P_4$ and $P_5$, which correspond to the peaks of photoluminescence and proved to be radiative defects.

Thus, according to the method of this invention there could be observed nonradiative defects directly. And it was found that the photoluminescence method affords information on radiative defects, while the method of this invention provides information on nonradiative defects.

Figure 17A:
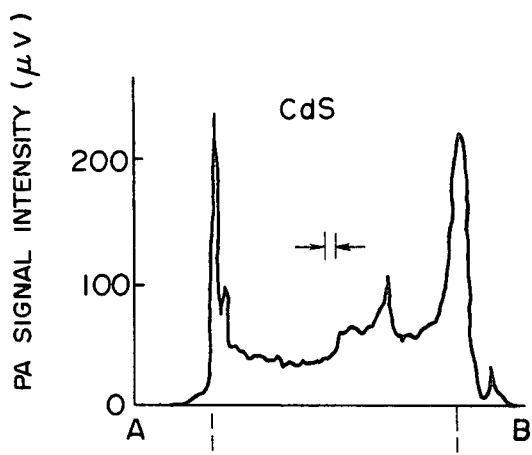
FIG. 17(a) illustrates a spatial distribution of crystal defects obtained by the apparatus of this invention.
Figure 17B:
FIG. 17(b) is an exact reproduction of a crystal structure photograph.

Furthermore, there were observed broad peaks of a deep level at about 550 nm to about 700 nm, which are some defect in the crystal. There was checked a spatial distribution of such deep level defects, the results of which are shown in FIG. 17. As the source of excitation energy there was used a He-Ne laser with a wavelength of 632.8 nm and an output of 6 mW, and the jig carrying the sample was scanned mechanically. FIG. 17(b) illustrates an exact reproduction of a crystal structure photograph, wherein the parts which are seen as white spots are mechanical defects. FIG. 17(a) shows photoacoustic signal intensity taken on line A-B of FIG. 17(b). The defects at both ends of the crystal and the defect at the central portion thereof observed in the optical photographic image on the line A-B corresponded to the peaks of photoacoustic signal. The other components than the peaks in FIG. 17(a) are defects throughout the crystal and are invisible in the optical photographic image.

In FIG. 18, Si sample of (100) crystal face was evaluated using as the source of excitation energy a He-Ne laser with a wave length of 632.8 nm and an output of 6 mW.

Figure 18A:
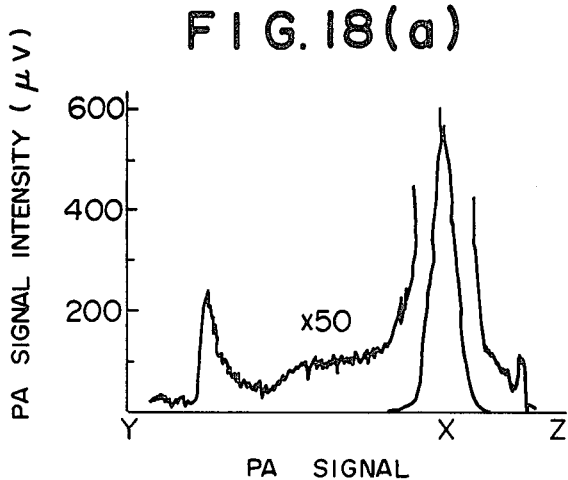
FIG. 18(a) illustrates the intensity of photoacoustic signals from crystal defects obtained by the apparatus of this invention.

FIG. 18(a) shows the distribution of photoacoustic signal intensity on line Y-Z of the sample.

Figure 18B:
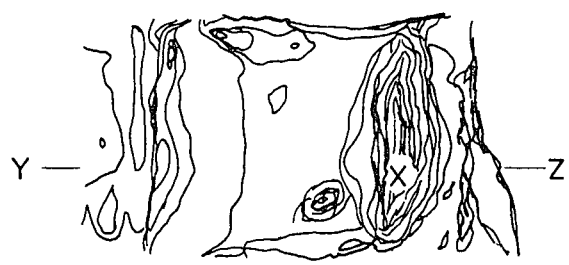
FIG. 18(b) is a photoacoustic topograph.

FIG. 18(b) shows the spatial distribution of FIG. 18(a) in terms of a photoacoustic topograph throughout the surface of the sample using contour lines.

Figure 18C:
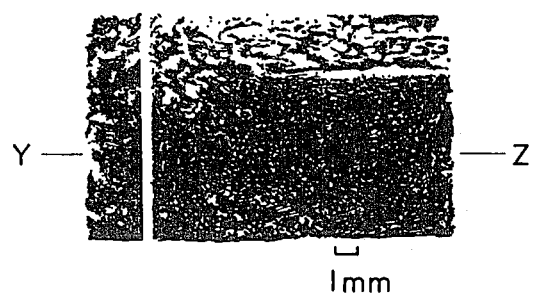
FIG. 18(c) is an exact reproduction of an X-ray photograph of a crystal structure.

FIG. 18(c) illustrates an exact reproduction of X-ray photograph of the crystal structure of the same sample, in which there are found portions corresponding in defects distribution to the photoacoustic topograph. And those invisible in Fig. 18(c) could be observed by the photoacoustic topograph like the defects indicated with the reference mark X in FIG. 18(b).

Figure 19:
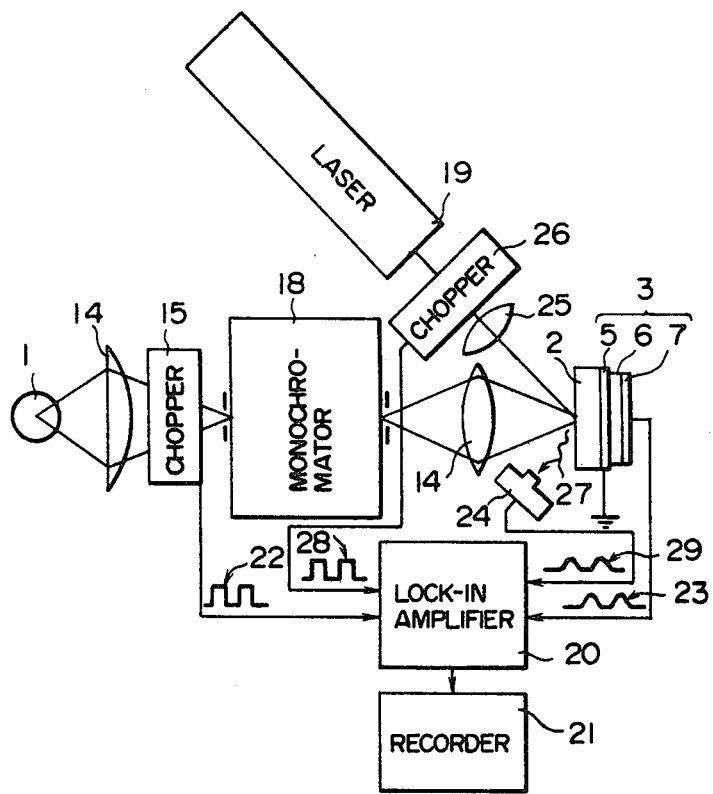
FIG. 19 illustrates another embodiment of a crystal defects analyzer.

In FIG. 19 there is shown, as another embodiment, reference numerals the same with the reference numerals in FIGS. 1 to 18 designate parts similar to those in FIGS. 1 to 18. A crystal defects analyzer of this embodiment is constructed so that the change in the course of time of the energy distribution of crystal defects and the change in the course of time of photoluminescence can be observed simultaneously while allowing crystal defects to be produced. As an example, there was observed a photoacoustic signal from the sample 2 using a 150 W tungsten lamp as the source of excitation energy 1, using the lens system 14 with a focal point of about 10 cm to condense a light beam to below 100 µm, further using the monochromator 18 with a resolution of about 20 Å to 30 Å and at a chop frequency of the chopper 15 of about 300 Hz. At the same time, as an example, a red multiline output of Kr+ laser was used as a laser 19 and crystal defects were allowed to be produced by condensing an output via a chopper 26 by a lens 25 with a focal point of about 1 cm and irradiating it onto the surface of the sample at an intensity of about 3 kW/cm². The chopper 26 was always opened in this case. In FIG. 19 the reference numerals 22 and 28 are reference signals, 23 is a photo-acoustic (PA) signal and 29 is a PL signal.

Table 2 shows the results of the above experiment with respect to GaAs and InP samples which were evaluated.

TABLE 2

List of samples of GaAs and InP used in the experiment

| | Sample Number | Substrate | | | Epitaxial Layer | | |
|---|---|---|---|---|---|---|---|
| | | Dopant | EPD* | n** | Dopant | n** | Film Thickness (µm) |
| GaAs (100) | S-1 | Si | $<10^4$ | $\sim 1 \times 10^{18}$ | S | $\sim 1 \times 10^{17}$ | $\sim 10$ |
| | S-2 | Si | $\sim 10^5$ | $\sim 5 \times 10^{18}$ | S | $\sim 1 \times 10^{17}$ | $\sim 10$ |
| InP (100) | S-4 | Fe | $\sim 10^5$ | SI*** | — | — | — |
| | S-5 | Sn | $\sim 10^5$ | $>3 \times 10^{18}$ | — | — | — |
| | S-6 | S | $<10^3$ | $\sim 5 \times 10^{18}$ | — | — | — |

*EPD: etch pit density (cm$^{-2}$)
**n: carrier concentration (cm$^{-3}$)
***SI: semi-insulating substrate In Table 2 there are shown dopant, etch pit density and carrier concentration of the substrate and epitaxial layer with respect to each of the samples. The crystal face is (100) face in both GaAs and InP.

Figure 20:
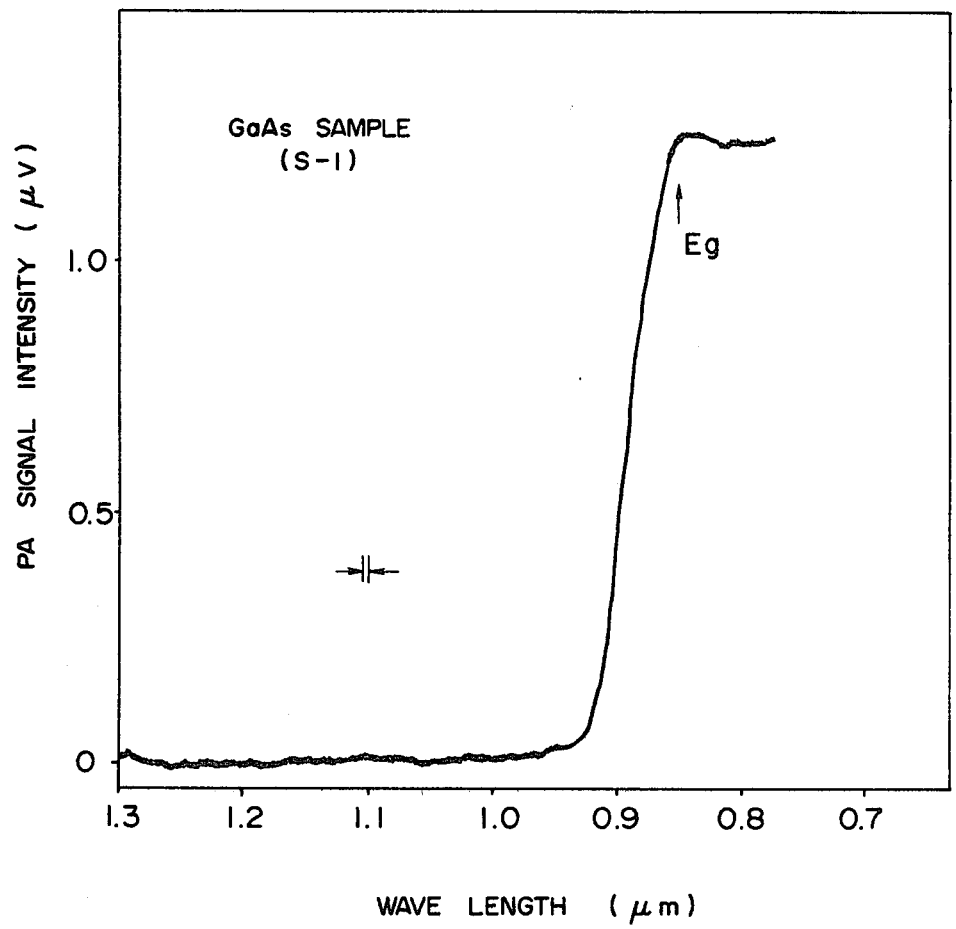
FIG. 20 illustrates a photoacoustic spectrum of GaAs sample S-1 in normal state.

FIG. 20 shows the relationship between the photoacoustic signal intensity and the excitation lightwave length characteristic (hereinafter referred to as the "photoacoustic spectrum") of the GaAs sample S-1 in normal state, in which Eg designates a band gap.

Figure 21:
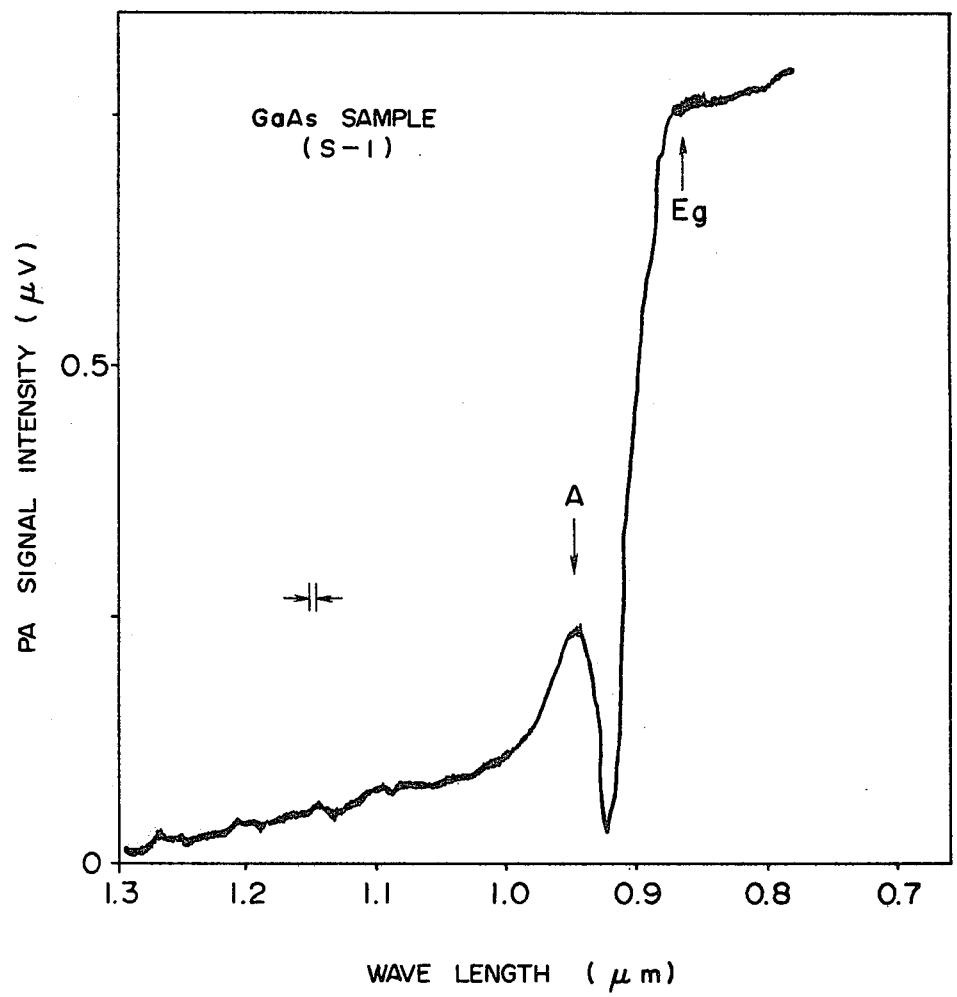
FIG. 21 illustrates a photoacoustic spectrum of GaAs sample S-1 as oxygenated.

In FIG. 21 there is shown the photoacoustic spectrum after the same GaAs sample S-1 was held in oxygen atmosphere (about 0.1 Torr, sample temperature about 200° C.) for about 6 hours. In this case, signal A appeared remarkably, which signal disappeared when the surface of the sample was etched about 2000 Å. Consequently, this signal proved to be a signal induced by a crystal defect on the crystal surface layer.

Figure 22:
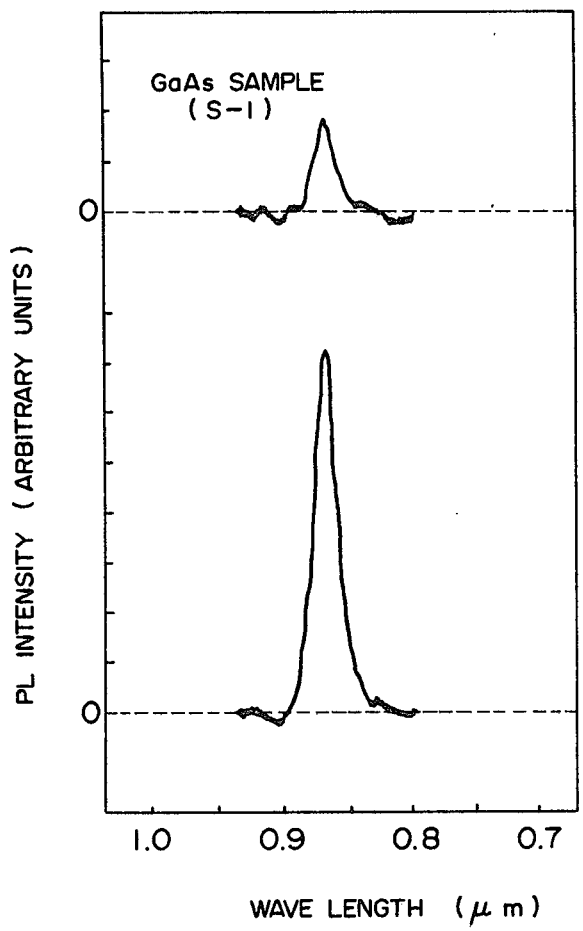
FIG. 22 illustrates a photoluminescence of GaAs sample S-1 as oxygenated and etched.

FIG. 22 shows data of photoluminescence when the same GaAs sample S-1 was subjected to the above oxygenation (its characteristic is depicted at the upper portion of FIG. 22) and also after it was etched in the above-mentioned manner (its characteristic is depicted at the lower portion of FIG. 22). For the observation of photoluminescence, as shown in FIG. 19, the sample was excited by a He-Ne laser of 6 mW output as the laser 19 and a photoluminescence light 27 was observed by Si photodiode of photo detector 24. As shown in FIG. 22, the photoluminescence intensity lowers, which when etched reverts to the state before the oxygenation. Thus it has become clear that the crystal defect which causes photoacoustic signal A has deteriorated photoluminescence.

Figure 23:
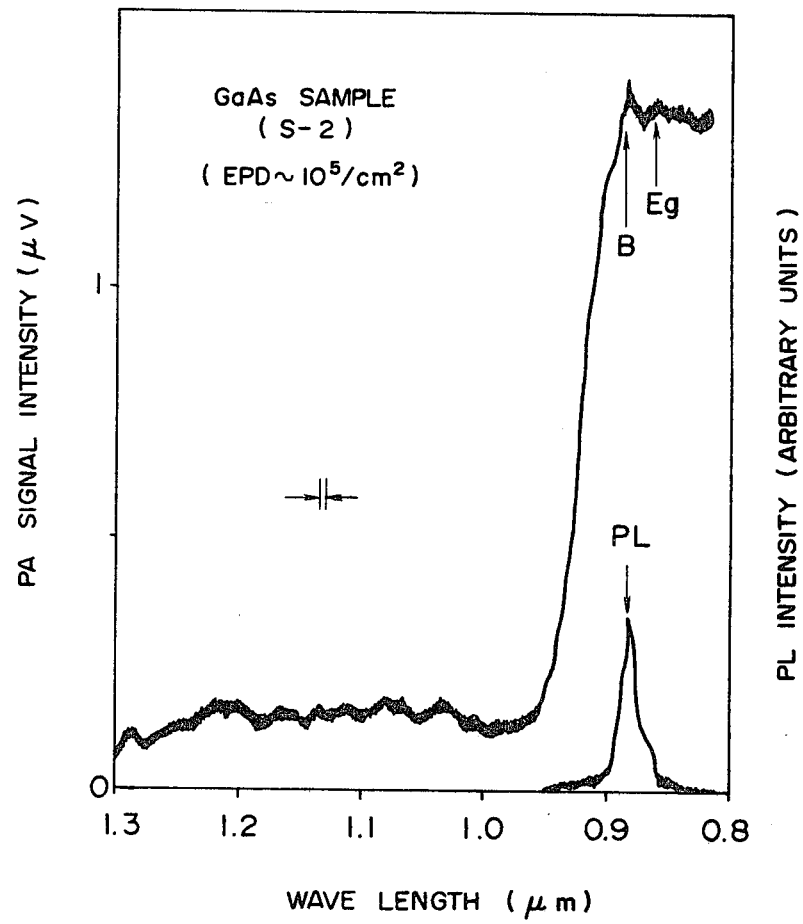
FIG. 23 illustrates a photoacoustic spectrum of GaAs sample S-2.

FIG. 23 shows the dependency of photoacoustic signal and photoluminescence upon wave length with respect to the GaAs sample S-2 shown in Table 2, from which it is seen that, as compared with the GaAs sample S-1, the other sample S-2 is higher in etch pit density, i.e. dislocation density.

From the comparison between FIGS. 20 and 23 it has been found that the photoacoustic signal B (near 0.89 $\mu$m) and photoacoustic signals distributed at 1.0-1.3 $\mu$m provide information on dislocation. It was also found that the photoluminescence peak PL observed at the same time was close to the photoacoustic signal B and the dislocations in GaAs absorbed the photoluminescence light.

Figure 24:
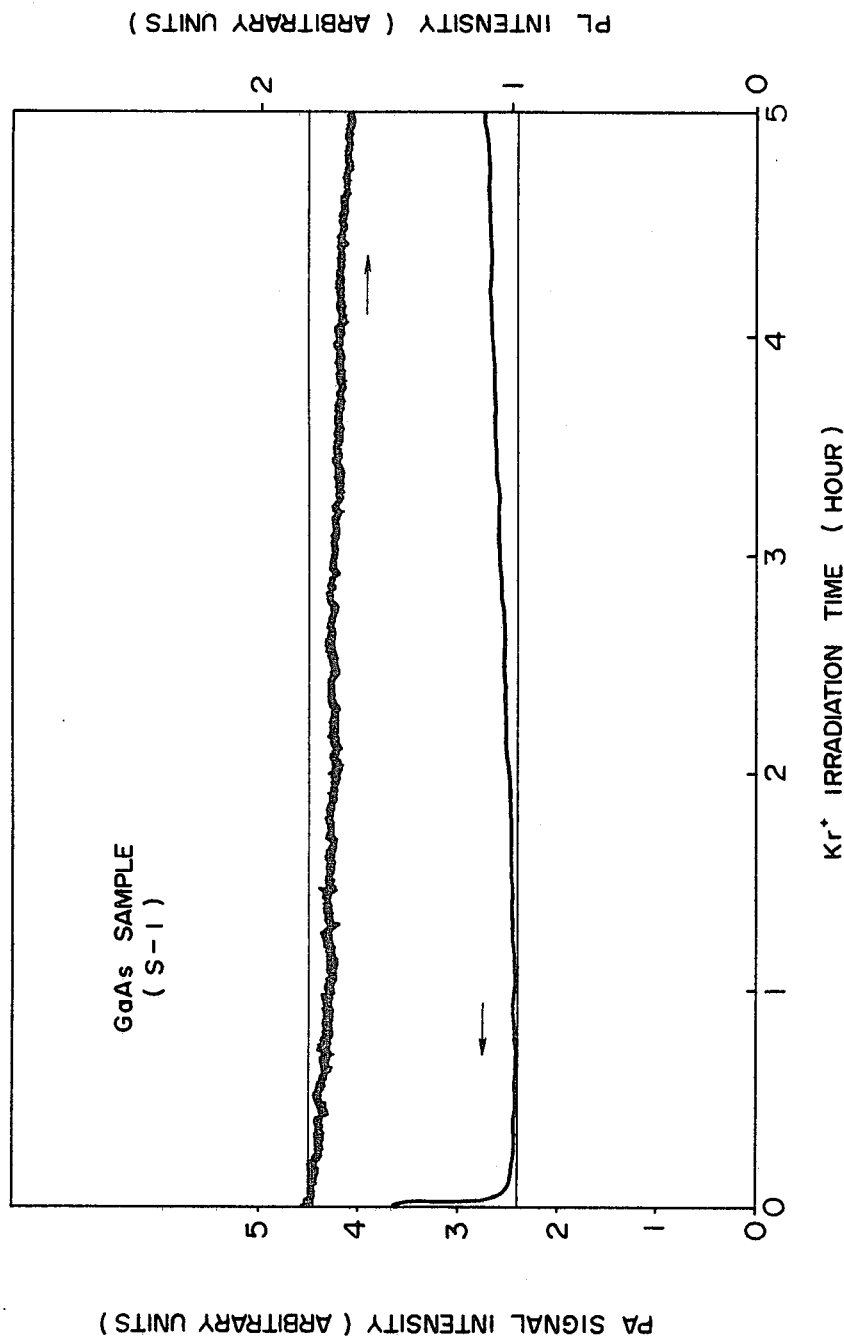
FIG. 24 illustrates changes in photoacoustic signal intensity and photoluminescence intensity of GaAs sample S-1 as photo-damaged.
Figure 25:
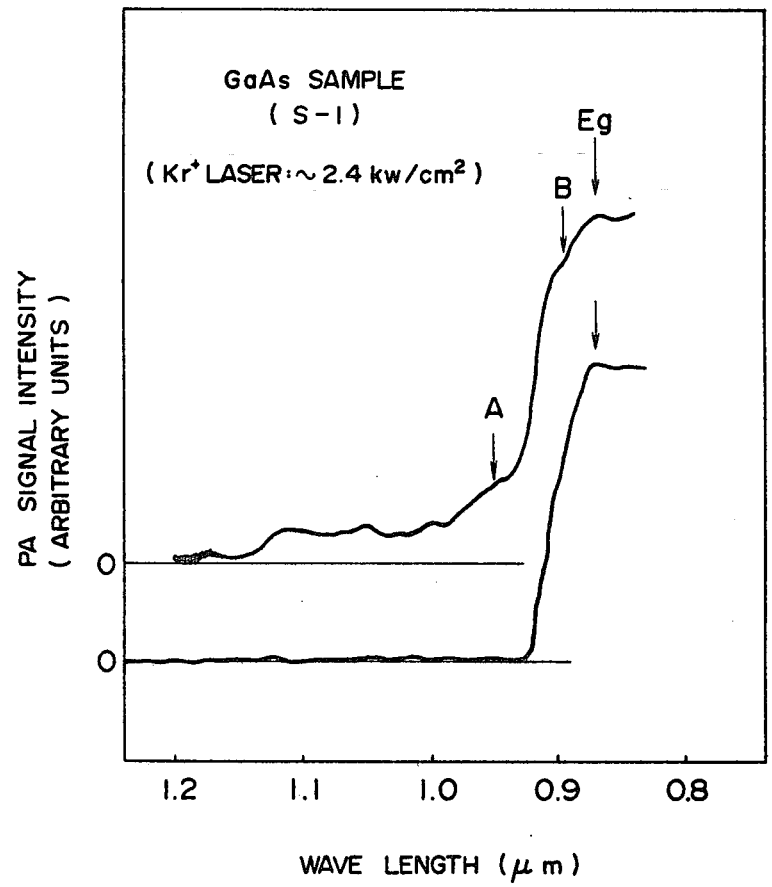
FIG. 25 illustrates changes in photoacoustic spectrum of GaAs sample S-1 before its photo-damage and after photo-damage for 3 hours.

FIG. 24 shows data obtained by photodamaging the GaAs sample S-1 in the air at room temperature through irradiation of Kr+ laser in the manner previously noted and at the same time observing the photoluminescence intensity. In this experiment, the chop frequency of the chopper 26 in the embodiment shown in FIG. 19 was set at about 300 Hz. As shown in FIG. 24, it has been found that the photo damage brings about a decrease in photoluminescence intensity and an increase in photoacoustic signal intensity. As shown in FIG. 25, there were checked the change in photoacoustic spectrum (its characteristic is shown at the lower portion of FIG. 25) before irradiation of Kr+ laser and the change in photoacoustic spectrum (its characteristic is shown at the upper portion of FIG. 25) after 3 hours' irradiation of the same laser. The data before irradiation of Kr+ laser are the same as the data shown in FIG. 20, but after 3 hours' irradiation of Kr+ laser there appeared the signal B indicative of the creation of dislocation shown in FIG. 23, signals distributed at 1.0 to 1.2 $\mu$m and the signal A generated in the oxygenation shown in FIG. 21, and thus the occurrence of crystal defects was observed.

Figure 26:
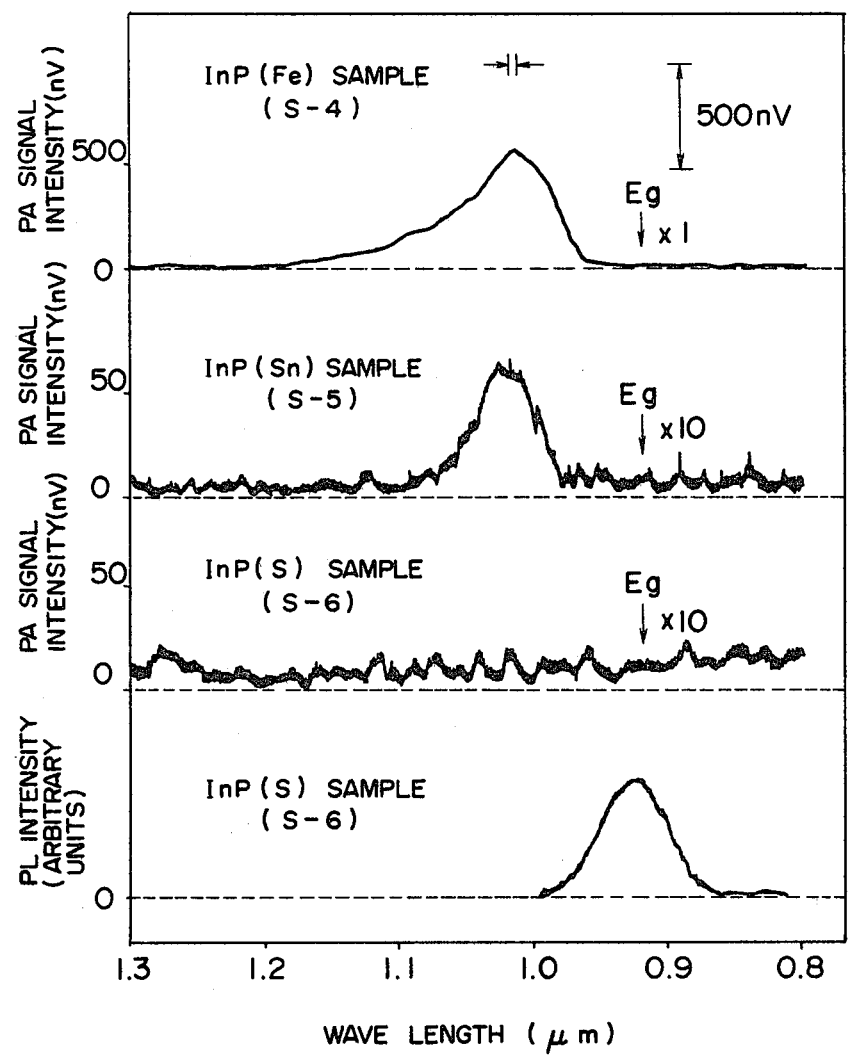
FIG. 26 illustrates photoacoustic spectra of InP samples S-4, S-5, S-6 and photoluminescence of sample S-6.

FIG. 26 shows an example of measurement of photoacoustic spectra of the InP crystal samples S-4, S-5, S-6 shown in Table 2 and photoluminescence of the sample S-6. This measurement was done under the same conditions as in FIG. 23 which shows a measurement example on GaAs, but the results are greatly different. It was found that a photoacoustic signal was not existent at the wave lengths close to photoluminescence. Consequently, it was found that InP, as compared with GaAs, contained less crystal defects absorbing luminescence light.

Figure 27:
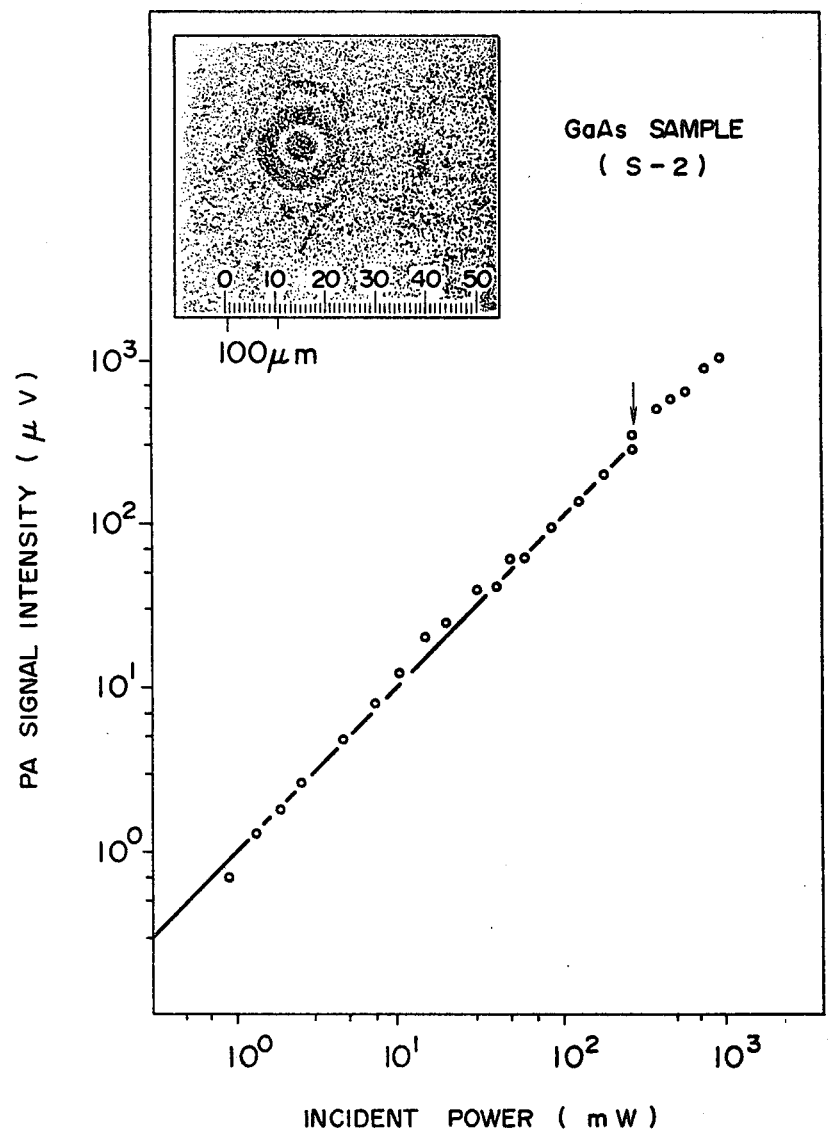
FIG. 27 illustrates the dependency of the photoacoustic signal intensity of GaAs sample S-2 upon the exciting light power.

In FIG. 27 there was measured the dependency of the photoacoustic signal intensity upon the power of Kr+ laser with respect to the GaAs sample S-2. It was observed that the photoacoustic signal intensity was proportional to the power and that the crystal dissolved at the point indicated with the arrow and the photoacoustic signal intensity changed discontinuously.

It goes without saying that the invention is not limited to the embodiments shown in FIGS. 1 through 27. Any apparatus may be used if only they are provided with excitation means for exciting crystals to be analyzed and with means for converting acoustic changes into electrical changes disposed in close adherence to the crystals to be analyzed through the medium of a filter layer. For example, the excitation means may be a light source such as a light emitting lamp or laser, or an electron irradiator adapted to emit electrons, or a particle irradiator adapted to emit particles. For a semiconductor sample, an excited state may be created by injection of electrons or holes from the PN junction.

The acousto-electric conversion means may be formed of a material which exhibits piezo-electric or pyroelectric characteristics. Alternatively, there may be performed an electric conversion using acoustic changes of the PN junction in a semiconductor material or acoustic changes in MOS diode or MOS FET.

Since the crystal defects analyzer of this invention, as compared with the prior art apparatus, can attain higher response and sensitivity, smaller size, higher resistance to vibration and superior operationality, its industrial value is very high.

We claim:

1. A crystal defects analyzer comprising: excitation means for projecting light, electrons or particles on a face of a sample to be analyzed to excite said sample, a thin flexible acousto-electric transducer for converting acoustic waves or elastic strain within the sample into electrical signals, a thin flexible conductive noise-free filter layer bonding said acousto-electric transducer to the entire face of the sample opposite that exposed to said excitation means so that said acousto-electric transducer changes its shape according to deformation of the sample, said filter layer functioning to intercept light, electrons or particles emitted by said excitation means and to transmit acoustic waves or elastic strain produced within the sample by the excitation, means for modulating the amplitude of the light, electrons or particles emitted by said excitation means so as to excite the sample intermittently at a frequency which does not coincide with the resonance frequency of said acousto-electric transducer or an integer multiple thereof and means for holding the sample with said acousto-electric transducer bonded thereto by said filter layer in a manner to minimize acoustic coupling between said holding means and the sample, filter layer and acousto-electric transducer, the thickness of said filter layer being 3000 and 5000 angstroms and the thickness of said acousto-electric transducer being between several microns and several tens of microns, so that the sample, said filter layer and said acousto-electric transducer are allowed to change their integrated shape freely with the result that said acousto-electric transducer conducts the acousto-electric conversion with respect to the modulation frequencies in a broad band.

2. A crystal defects analyzer according to claim 1 wherein a further conductive layer is bonded to the face of said acousto-electric transducer opposite that bonded to said filter layer, output terminals being converted to said filter layer and said further layer.

3. A crystal defects analyzer according to claim 2, wherein the thickness of said further conductive layer is between 3000 and 5000 angstroms.

4. A crystal defects analyzer according to claim 1, wherein the total thickness of said filter layer and said acousto-electric trasducer does not exceed about 100 microns and the total thickness of the sample, said filter layer and said acousto-electric transducer does not exceed about 1 mm.

5. A crystal defects analyzer according to claim 1, wherein said excitation means comprises a light source for irradiating light onto the crystal surface of said sample.

6. A crystal defects analyzer according to claim 5, wherein said light source is a lamp and there is provided a lens for condensing light emitted from said lamp.

7. A crystal defects analyzer according to claim 5, wherein said light source is laser.

8. A crystal defects analyzer according to claim 1, wherein said excitation means comprises an electron irradiator.

9. A crystal defects analyzer according to claim 1, wherein said excitation means comprises a particle irradiator.

10. A crystal defects analyzer according to claim 1, further comprising means for rendering the light or electrons or particles emitted from said excitation means beam-like.

11. A crystal defects analyzer according to claim 10, further comprising means for deflecting the resulting beam of light or electrons or particles to scan the surface of the sample.

12. A crystal analyzer according to claim 1 further comprising means for scanning said sample mechanically.

13. A crystal defects analyzer according to claim 1, further comprising means for changing the energy level of the light or electrons or particles emitted from said excitation means.

14. A crystal defects analyzer according to claim 1, wherein said filter layer is deposited on a face of said acousto-electric transducer and is bonded to the sample by a bonding layer.

15. A crystal defects analyzer according to claim 1, wherein said filter layer is deposited on a face of said acousto-electric transducer and is held against said sample by vacuum.

16. A crystal defects analyzer according to claim 1, wherein said filter layer comprises a first layer deposited on said acousto-electric transducer, and a second layer deposited on the sample, said first and second layers being united by thermo-compression bonding.

17. A crystal defects analyzer according to claim 1, wherein said holding means comprises a jig bonded to one edge of at least one of said filter layer and said acousto-electric transducer.

18. A crystal defects analyzer according to claim 1, wherein said holding means comprises a U-shaped jig bonded to opposite edges of said acousto-electric transducer.

19. A crystal defects analyzer comprising: first excitation means for projecting light, electrons or particles on a face of a sample to be analyzed to excite said sample, a thin flexible acousto-electric transducer for converting acoustic waves or elastic strain within the sample into electrical signals, a thin flexible conductive noise-free filter layer bonding said acousto-electric transducer to the entire face of the sample opposite that exposed to said excitation means so that said acousto-electric transducer changes its shape according to deformation of the sample, said filter layer functioning to intercept light, electrons or particles emitted by said excitation means and to transmit acoustic waves or elastic strain produced within the sample by the excitation, means for modulating the amplitude of the light, electrons or particles emitted by said excitation means so as to excite the sample intermittently at a frequency which does not coincide with the resonance frequency of said acousto-electric transducer or an integer multiple thereof, and second excitation means for concurrently irradiating said face of the sample at a different angle to induce photoluminescence, and photo-detector means for detecting the photolusminescence produced by said second excitation means means for holding the sample with said acousto-electric transducer bonded thereto by said filter layer in a manner to minimize acoustic coupling between said holding means and the sample, filter layer and acousto-electric transducer, the thickness of said filter layer being between 3000 and 5000 angstroms and the thickness of said acousto-electric transducer being between several microns and several tens of microns, so that the sample, said filter layer and said acousto-electric transducer are allowed to change their integrated shape freely with the result that said acousto-electric transducer conducts the acousto-electric conversion with respect to the modulation frequencies in a broad band.

20. A crystal defects analyzer according to claim 19, wherein said second excitation means is laser.

21. A crystal defects analyzer according to claim 19, wherein said second excitation means is a source of an electron beam.

22. A crystal defects analyzer according to claim 19, wherein said second excitation means is a source of an ion beam.

23. A crystal defects analyzer according to claim 19, further comprising means connected to said acousto-electric transducer and said photo-detector means and coordinating the outputs of said acousto-electric transducer and said photo-detector means.

24. A crystal defects analyzer according to claim 23, wherein said coordinating means comprises an amplifier connected to said acousto-electric transducer and said photo-detector and recording means connected to said amplifier.

* * * * *